US008070935B2

(12) United States Patent
Choi et al.

(10) Patent No.: US 8,070,935 B2
(45) Date of Patent: Dec. 6, 2011

(54) APPARATUS FOR ANALYZING TIN COMPOUNDS IN LIQUID SAMPLES AND METHOD FOR ANALYZING TIN LEVELS USING THE SAME

(75) Inventors: Yong Su Choi, Seoul (KR); Seok Won Hong, Seoul (KR); Sang Hyup Lee, Gunpo-si (KR); Hyung Joo Kim, Seoul (KR); Chang Ho Choi, Uijengbu-si (KR); Bong Geun Jeong, Ulsan (KR)

(73) Assignee: Korea Institute of Science and Technology, Seoul (KR)

( * ) Notice: Subject to any disclaimer, the term of this patent is extended or adjusted under 35 U.S.C. 154(b) by 1089 days.

(21) Appl. No.: 11/974,319

(22) Filed: Oct. 12, 2007

(65) Prior Publication Data

US 2008/0230400 A1     Sep. 25, 2008

(30) Foreign Application Priority Data

Mar. 21, 2007   (KR) .................. 10-2007-0027532

(51) Int. Cl.
*G01N 27/333*    (2006.01)
(52) U.S. Cl. .................... 205/789.5; 205/775
(58) Field of Classification Search ............. 205/775, 205/789, 789.5; 204/409–412, 416–418
See application file for complete search history.

(56) References Cited

U.S. PATENT DOCUMENTS

| 4,610,169 A | 9/1986 | Clavell, Jr. ............ 73/863.12 |
| 2003/0019748 A1* | 1/2003 | Viltchinskaia et al. ....... 204/400 |
| 2006/0276666 A1 | 12/2006 | Honda et al. .............. 556/87 |

FOREIGN PATENT DOCUMENTS

| JP | 58171667 A | 10/1983 |
| JP | 07128318 A | 5/1995 |
| JP | 2000162181 A | 6/2000 |
| KR | 1019940007529 A | 3/2009 |

OTHER PUBLICATIONS

Achterberg et al. "Stripping voltammetry for the determination of trace metal speciation and in-situ measurements of trace metal distributions in marine waters," Analytic Chimica Acta 400 (1999) 381-397.*

(Continued)

*Primary Examiner* — Alex Noguerola
(74) *Attorney, Agent, or Firm* — Ohlandt, Greeley, Ruggiero & Perle, LLP

(57) ABSTRACT

An apparatus for a continuous, automated quantitation of tin compounds in liquid samples and a method for quantitative analysis based on the said apparatus are provided herein. The inventive apparatus acidifies liquid samples and in case organotin compounds are present in the sample, a selective UV irradiation converts the organotin compounds into inorganic tin. The inventive apparatus quantitates this inorganic tin by means of electrochemical methods. The apparatus and method of the present invention allow quantitative analyses of trace amounts of organic and inorganic tin compounds present in liquid samples by converting organotin, a form unsuited for measurement, into inorganic tin, a form amenable to measurements and performing electrochemical analysis. Above all, the present invention affords the construction of an automated, continuous analysis system, making unnecessary additional manual operations and reducing labor costs. The present invention also provides an apparatus for converting organotin compounds into inorganic tin.

6 Claims, 12 Drawing Sheets

OTHER PUBLICATIONS van den Beg et al., "Electroanalysis for Organotin in Natural Waters including Sea-water by Cathodic Stripping Voltammetry," Analyst, Jun. 1991, vol. 116.*

Hoch, "Organotin compounds in the environment—an overview," Applied Geochemistry 16 (2001) 719-743.* van den Berg et al., "Determination of Tin in Sea Water by Adsoprtive Cathodic Stripping Voltammetry," Analytic Chimica Acta, 222 (1989) 43-54.*

Heppler et al., "Determination of tin traces in water samples by adsorptive stripping voltammetry," Analytic Chimica Acta 319 (1996) 19-24.*

Economou et al., "Mercury film electrodes: developments, trends and potentialities for electroanalysis," Analyst, 2003, 128, 205-212.*

Rodriguez-Gonzalez, et al.; "Determintaion of butyltin compounds in coastal sea-water samples using isotope dilution GC-ICP-MS;" Journal of Analytical Atomic Spectrometry, 2002 (v. 17—pp. 824-830).

* cited by examiner

APPARATUS FOR ANALYZING TIN COMPOUNDS IN LIQUID SAMPLES AND METHOD FOR ANALYZING TIN LEVELS USING THE SAME

CROSS-REFERENCES TO RELATED APPLICATIONS

The present application claims priority to Republic of Korea patent application No. 10-2007-0027532 filed Mar. 21, 2007.

FIELD OF THE INVENTION

The present invention relates to an apparatus and method for a continuous and automatic analysis of liquid samples containing organotin compounds.

BACKGROUND ART

The use of organotin compounds has grown rapidly since their commercialization in 1936 both in terms of quantity and scope. These compounds are widely used in such areas as stabilizers for plastics including polyvinyl chlorides (PVCs), industrial catalysts, pesticides, antimicrobials and wood preservatives. Since the 1960's, tributyltin (TBT) has been added to paint coatings for ships and marine structures as antifouling agents to prevent underwater creatures from attaching themselves. There has been growing concerns, however, about the harmful nature of organotin compounds since many of these are toxic and able to disrupt normal growth even when traces are released into the ecosystem. Tributyltin, a representative organotin pollutant of the sea, is polluting marine ecosystems on a global scale. It has been reported to inhibit the growth of oysters, mussels and bivalves. Since the early 1980's, tributyltin has been also known to cause imposex in gastropods, in which formation of male genitalia occurs in females accompanied with a loss of reproductive function. Meanwhile, other toxic organotin compounds such as triphenyltin and tricyclohexyltin are causes for concern as well.

The diplomatic conference held in October, 2001 at the international maritime organization (IMO) has adopted the antifouling system (AFS) convention that regulates the use of TBT antifouling agents on ships. Taking momentum from this convention, the Korean government is in the process of incorporating the contents of this convention into domestic law.

Already, the Ministry of Environment of Korea issued an announcement (No. 2003-163, Sep. 16, 2003) listing antifouling paints containing tributyltin as "chemicals of which production, import or use are either banned or subject to restrictions". In addition, a total ban on tributyltin-containing antifouling paints has been in effect since Nov. 13, 2003 for all ships registered in Korea including ocean liners and deep-sea fishing vessels.

As described above, organotin compounds can cause severe damage to ecosystems and their concentrations in the environment constantly vary according to biological (e. g., metabolism) and non-biological (season, ocean currents) factors. However, research has been lacking on apparatuses and methods for a facile, accurate and continuous determination of these compounds. At the moment, there are no patent applications directed to systems or methods for determining organotin compounds in Korea.

Although there are some methods of analysis available for quantitating organotin compounds in liquid samples (titration, gas chromatography, etc.), none of these methods have been automated so far. Gas chromatography (GC) is the method most generally used among these. For instance, U.S. Pat. No. 4,610,169 describes an apparatus for concentrating organotin compounds in gaseous samples by means of a variable temperature trap for determining organotin levels. Apparently, this still leaves a strong need for a measuring device that does not require such pretreatment steps. An article from the Journal of Analytical Atomic Spectrometry (vol. 17 (2002), pp 824-830) discloses a method based on gas chromatography and mass spectrometry for mono-, di- and tributyltin in seawater. This method involves the cumbersome step of extraction with organic solvents for gas chromatography and mass spectrometry analyses. In addition, since this method requires a tin isotope $^{119}$Sn for analysis, it can be costly. In US patent publication No. 2006/0276666, a method for treating liquid samples contaminated with organotin compounds, organotin compounds are likewise extracted with organic solvents followed by gas chromatography for the evaluation of decontamination efficiency. Meanwhile, the Korean official test method for marine environment describes a GC-based method for determining levels of organotin compounds. In this method, organotin compounds from samples are extracted with methylene chloride, concentrated and derivatized with Grignard reagents, followed by filtration through a Florisil® column to remove interfering substances. This column eluate is then subject to separation with GC and finally the components are detected using a flame photometric detector (FPD).

Although gas chromatography, as shown above, is the conventional method for analyzing organotin compounds, it has important shortcomings as well. GC involves various, complicated pre-treatment steps which are cumbersome to manual operators, making automation a difficult goal. In addition, losses can occur during the stages of extraction and concentration and such manual operations are prone to wide variation in data quality depending on the operator. Furthermore, GC equipments are costly. Considering the extremely small quantities of analyte samples injected in GC, the reliability of data obtained from GC is further diminished when such shortcomings as mentioned above are taken into account.

Even if methods other than GC were available for determining organotin levels so that the shortcomings associated with GC could be overcome, such methods would still suffer from their inability to continuous concentration measurements as well as wide discrepancies in measurements arising from the different capabilities of individual operators as long as they involve unautomated steps including pre-treatment of samples. Thus, the demand for automated systems capable of an accurate, continuous and convenient determination of trace levels of organotin in liquid samples still remains unanswered.

SUMMARY OF THE INVENTION

The present invention addresses these problems stated above. One object of the present invention is to provide a measuring apparatus with which an unmanned, automated analysis of liquid samples containing organotin compounds can be conducted automatically and continuously. The inventive apparatus and method convert organotin compounds into inorganic tin compounds, a form suitable for electrochemical analyses, using a pre-treatment procedure consisting acidification and ultraviolet (UV) irradiation. The analysis of organotin compounds in the present invention is characterized in that the whole process is automated and does not require additional manipulation.

The inventive apparatus comprises a sample reservoir for storing liquid samples, an acidifier a sample reservoir for storing liquid samples; an acidifier for injecting acid into the said liquid sample, delivered from the said sample reservoir, to adjust the acidity of the said sample until a predetermined value is reached; a reactor for conducting electrochemical measurements on the said liquid sample after the acidification of the said sample by the said acidifier is complete; and a detector for detecting electrochemical signals generating from the said reactor.

In another aspect of the present invention, an apparatus for converting organotin compounds in liquid samples into inorganic tin compounds is provided. This apparatus comprises a sample reservoir for storing liquid samples; an acidifier for injecting acid into the said liquid sample so as to adjust the acidity of the said sample until a predetermined value is reached; an acidity detector for measuring the acidity of the said sample injected with acid and forwarding the measured acidity to the said acidifier so as to control the said acidifier; and an ultraviolet irradiator for irradiating the said sample upon completion of the said acidification with ultraviolet light.

The analytic principles of the present invention can be applied to inorganic tin compounds in liquid samples as well. A method for analyzing inorganic tin compounds may comprise the following steps of: (a) acidifying a liquid sample containing known concentration of inorganic tin by injecting acid so as to adjust the acidity of the said sample until a predetermined value is reached; (b) measuring voltammetric current for the acidified sample from step (a); (c) repeating the steps of (a) and (b) for various other liquid samples of known concentrations of inorganic tin and establishing a calibration curve correlating the measured current with inorganic tin concentration; (d) performing the acidification step of (a) on an unknown liquid sample; (e) measuring voltammetric current for the acidified unknown sample from step (d); and (f) determining the concentration of inorganic tin in the said unknown liquid sample by matching the current value obtained in step (e) against tin concentration from the said calibration curve of step (c).

In still another aspect of the present invention, the above analytic principles are applied to organotin compounds in the following order: (a) confirming the presence of organotin compounds within an unknown sample by acidifying the unknown sample and irradiating ultraviolet on it, followed by detecting the difference in the voltammetric current with or without UV irradiation; (b) determining the concentration of inorganic tin present in the said unknown sample by conducting the steps of the said method for analyzing inorganic tin on another batch of the same sample, wherein the said another batch of the unknown sample has not been subject to step (a) prior to being subject step (b); (c) acidifying still another batch of the same unknown sample by injecting acid and converting organo tin compounds within the said acidified batch into inorganic tin by irradiating the said batch with ultraviolet light, wherein the said still another batch of the unknown sample has not been subject to steps (a) and (b) prior to being subject step (c) and wherein the said acid injection continues until the acidity of the said sample reaches a predetermined value; (d) determining the combined concentration of organic and inorganic tin for the said still another batch of sample after step (c) by performing steps (e) and (f) from the said method for analyzing inorganic tin; and (e) subtracting the concentration value of step (d) from that of step (b).

BRIEF DESCRIPTION OF THE DRAWINGS

FIG. 3, 0 ppm; FIG. 4, 22 ppm; FIG. 5, 35 ppm and FIG. 6, 54 ppm, respectively). The observed current readings were respectively, 15.06 μA (FIG. 3, 0 ppm), 17.86 μA (FIG. 4, 22 ppm), 18.87 μA (FIG. 5, 35 ppm) and 21.26 μA (FIG. 6, 54 ppm).

DESCRIPTION OF THE EMBODIMENTS

Figure 1:
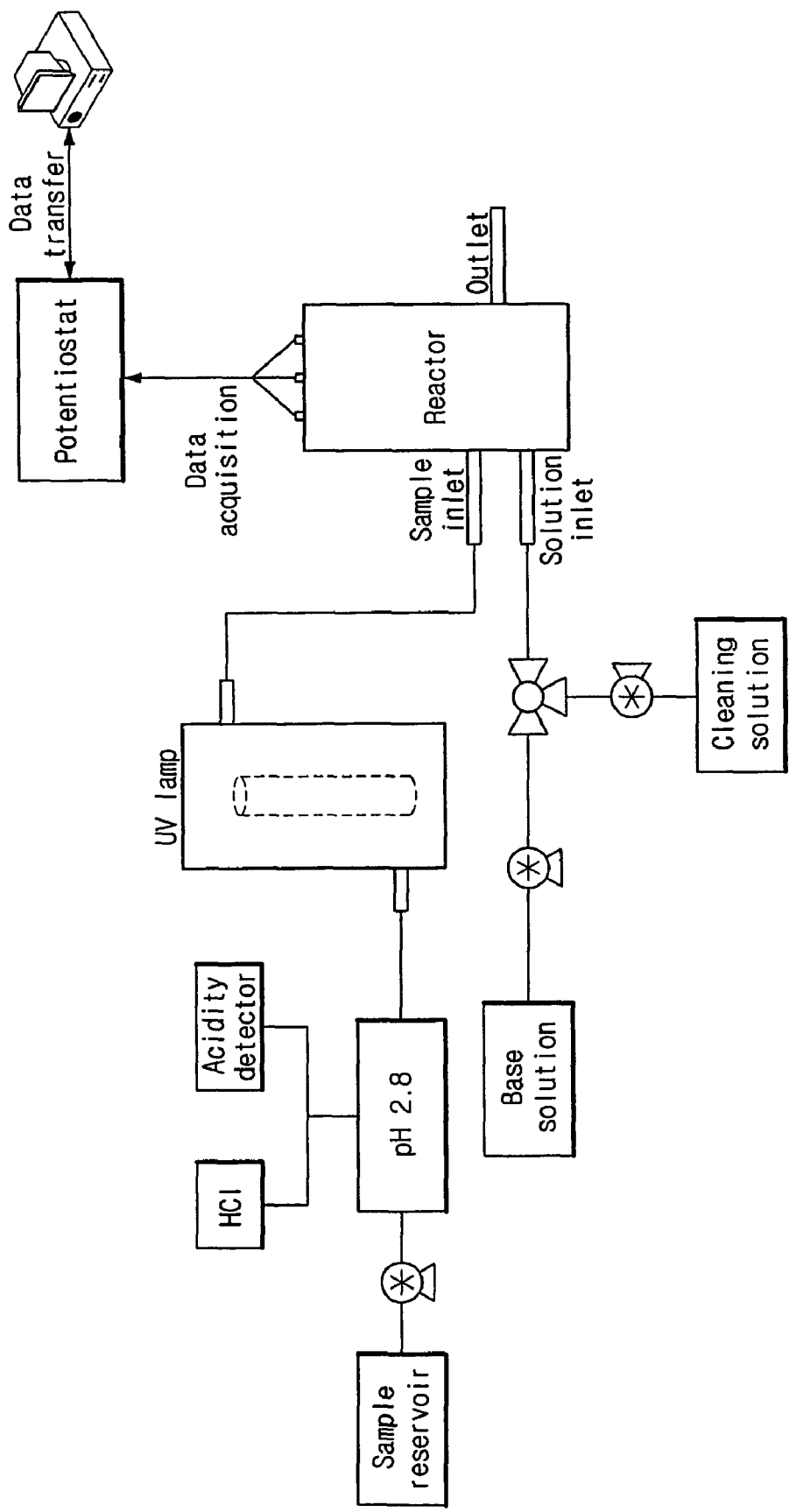
FIG. 1 is a schematic diagram showing an embodiment of the inventive apparatus for automated analysis of tin compounds in liquid samples.

The present invention provides an answer to problems stated above. One object of the present invention is to provide a measuring apparatus with which an unmanned, automated analysis of liquid samples containing organotin compounds can be conducted automatically and continuously. To afford electrochemical measurements, organotin compounds are converted into inorganic tin compounds by a pre-treatment procedure consisting of acidification and UV irradiation. The measuring apparatus of the present invention provides automatic analysis of tin samples without requiring additional, manual operation.

The characteristic features and advantages of the present invention will be described in detail in the following with reference to the attached drawings. However, before going into the description, it should be noted that the meanings and concepts of the terms used herein should be interpreted in view of the inventive idea, based on the principle that the inventor may appropriately define terms so as to best describe the invention. In addition, one should note that any detailed description on prior arts related to the present invention was left out in the case where such description was considered unnecessarily obscuring the subject matter.

To accomplish the objects listed above, the present invention provides an apparatus for analyzing tin compounds capable of electrochemically detecting inorganic tin compounds within liquid samples. In one embodiment of the present invention, a measuring apparatus is provided wherein the electrochemical method is stripping voltammetry. Stripping voltammetry mainly consists of four steps: the first step in which analytes are deposited and collected under a constant electrode potential at a mercury electrode or other microelectrode; the second step in which electrolysis takes place with current flow; the third step in which deposited analytes are stripped off from the electrode after the electrolysis is completed; and the fourth step in which the concentration of the dissociated analytes is determined by a suitable voltammetric method. Since analytes are concentrated in the electrolysis step, stripping voltammetry is suited to accurate quantitation of trace materials. One object of the present invention is to provide an unmanned apparatus that enables automatic, continuous determination by means of electrochemical methods including stripping voltammetry, of organotin levels present in trace amounts within liquid samples, without being vulnerable to variation in the capabilities of individual operators.

When the tin sample consists only of inorganic tin, which is amenable to electrochemical methods, the apparatus of the present invention comprises a sample reservoir, acidifier, reactor and a detector.

By "sample reservoir" it is meant herein a place in which unaltered samples, suitably diluted or concentrated samples are stored. These stored samples are delivered in the following step to the acidifier described below.

By "acidifier" is meant herein a device that acidifies the liquid sample supplied from the said sample reservoir by controlled release of acid into the sample until a predetermined acidity value is reached. The amount of acid released by the acidifier is regulated through a feedback control by means of a measuring device which detects either the concentration or activity of proton or some other physical property indirectly related to the acidity of the sample.

In the reactor of the inventive apparatus, electrochemical measurements take place on samples handed over from the said acidifier once acidification is complete; thus the said reactor serves as an electrochemical cell. In one embodiment of the present invention, an electrode and a potentiostat is installed in the said reactor. One embodiment of the said electrode comprises a glassy carbon main body with mercury attached on its tip. In another embodiment of the said reactor, an inlet and outlet are provided for controlling the inflow and outflow of the base solution and background solution used for electrochemical measurements.

The inventive apparatus for analyzing tin compounds in liquid samples is capable of organotin quantitation as well. In such case, the inventive apparatus additionally comprises an ultraviolet (UV) irradiator (See FIG. 1).

By "UV irradiator", it is meant herein a device that decomposes organotin compounds into inorganic tin compounds and organic molecules by irradiating ultraviolet light on liquid samples handed over from the said acidifier once the acidification is over. Liquid samples irradiated with UV by means of the said UV irradiator are delivered to the said reactor after the irradiation is complete. In one embodiment of the present invention, the UV irradiator can choose whether to irradiate the sample handed over from the said acidifier so that both inorganic and organotin compounds can be analyzed.

FIG. 1 illustrates one specific embodiment of the inventive apparatus. The apparatus shown in FIG. 1 uses stripping voltammetry for determining organotin levels. The sample stored in the sample reservoir shown in FIG. 1 is carried to the acidifier by conveyor means such as pumps. There, the sample is injected with hydrochloric acid until the pH reading by an acidity detector reaches a preset value. This acidity value is preferably pH 2.5-3.5 and more preferably, pH 2.8.

The acidified sample, which now has an acidity matching the preset value, is passed over to the UV irradiator (corresponding to the "UV lamp" in FIG. 1). UV irradiation at this stage can be omitted for liquid samples containing only inorganic tin compounds. In FIG. 1, the acidified liquid sample is constantly subject to UV while it is introduced from the bottom part of the said UV irradiator and passed out through an outlet located in the upper part, converting organotin compounds into inorganic tin.

After UV irradiation, the sample is handed over to the reactor for the analysis of inorganic tin by a flow pump. In the example shown in FIG. 1, a glassy carbon main body with a thin layer of mercury formed at the tip serves as the electrode for the reactor. In FIG. 1, the rectangular box with "base solution" written on it, contains the base solution, which is a mixture of mercury and tropolone. The base solution provides mercury required for forming the electrode. Through another inlet connected to the reactor, tropolone is introduced. Tropolone helps the adsorption of inorganic tin and potassium (KCl) or sodium chloride (NaCl) solutions, which are used as background solutions for voltammetric measurements, onto the thin layer of mercury formed at the tip of the glassy carbon main body. The inventive apparatus shown in FIG. 1 is equipped with a potentiostat. The part of the apparatus connected to the detector is indicated as "Data Acquisition".

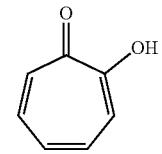

2-hydroxy-2,4,6-cycloheptatrien-1-on
tropolone

In the stripping voltammetric analysis of the present invention, the levels of inorganic tin compounds in the sample are determined first. Meanwhile, measurement of organotin samples begins with the step of converting organotin compounds into inorganic tin compounds, a form amenable to analysis. Independent to the said determination of inorganic tin levels, a separate batch, but otherwise identical sample is injected with hydrochloric acid by the acidifier of the present invention. The injection of hydrochloric acid is controlled by the acidity detector. The sample is then irradiated with ultraviolet light using the UV irradiator to break the bond between carbon and tin and decompose organotin compounds into inorganic tin and organic molecules. When the concentration of this inorganic tin is measured by stripping voltammetry, the concentration thus obtained is a sum of inorganic tin originally present in the sample and the inorganic tin converted from organotin compounds. The difference between this concentration value and that of the inorganic tin determined for the previous, untreated sample gives the amount of organotin compounds within the sample. The inventive apparatus is characterized in that it affords an automatic, continuous analysis, doing away with the need for manual operation of all constituent steps or monitoring of the apparatus. The apparatus of the present invention is most useful in the automated determination of organotin levels, but by all means it can also be used for detecting inorganic tin.

The present invention also provides an apparatus for automated conversion of organotin compounds into inorganic tin in liquid samples, comprising an acidifier and UV irradiator.

Figure 12:
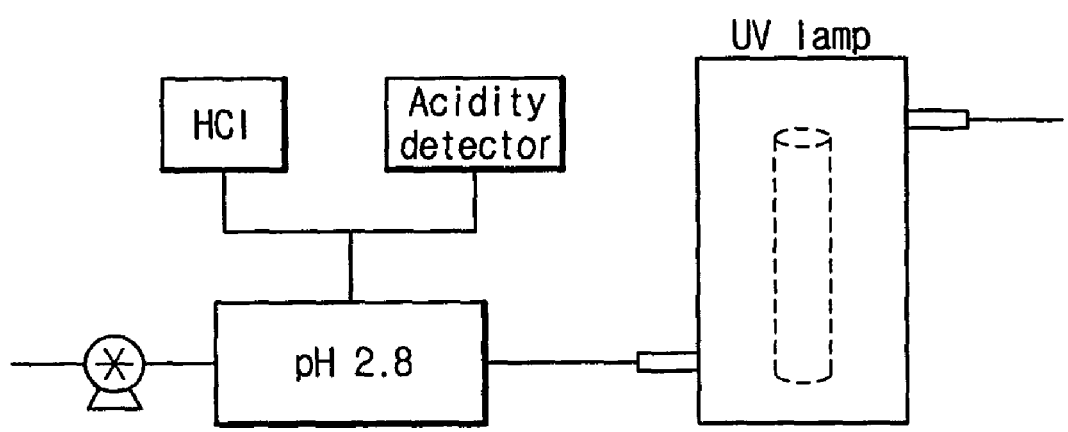
FIG. 12 shows the setup for converting organotin compounds into inorganic tin which comprises an acidifier and UV irradiator.

FIG. 12 is a schematic diagram for one embodiment of this apparatus. The inventive apparatus for conversion of organotin compounds is capable of continuous, automated transformation of organotin compounds, a form unsuited for direct quantitation, into inorganic tin without requiring manual intervention.

One aspect of this invention relates to a method for determining organotin or inorganic tin levels in liquid samples by means of the automated measuring apparatus of the present invention. The present invention also provides a method for converting organotin compounds into inorganic tin by means of the inventive conversion apparatus.

The present invention has the advantage of reduced measurement times since it determines the levels of organic and inorganic tin at a faster rate compared to other methods. A great number of steps prior to the actual measurement are required for other methods including pre-treatments and concentration of the sample. All such steps are automated in the present invention and therefore no special operations are necessary for measuring tin levels. Each step is automatically, continuously operated without the need for human intervention. This leads to reductions in cost and manpower as well as a boost in the reproducibility of measurements. In addition, since the present invention also provides an automated apparatus for converting organotin compounds, a difficult form for analysis, into inorganic tin, the time required for pre-treatment of samples for stripping voltammetry and other methods used in the analysis of organotin is reduced.

EXAMPLES

The present invention will be explained in more detail with reference to examples. The following examples are for the purposes of illustration only and by no means are intended to limit the scope of the present invention to embodiments described therein.

The examples below contain the following experiments: experiment one, forming a thin-layer mercury electrode for stripping voltammetry; experiment two, confirming the presence of organotin compounds in the sample (FIG. 2); experiment three, measuring currents from stripping voltammetric analyses of inorganic tin samples of various concentrations and plotting a calibration curve from these data (FIGS. 3, 4, 5, 6, 7); experiment 4, evaluating the calibration curve constructed in experiment 3 (FIGS. 8, 9, 10, 11); experiment 5, comparing the tin level obtained from voltammetry with an independently determined tin level for the same sample based on gas chromatography.

Example 1

Formation of a Thin Layer Mercury Electrode and Measurement Using the Same

A 20 mL aliquot of the base solution (0.8 mL of 0.009 N mercuric nitrate ($Hg(NO_3)_2$) and 80 µL of 10 mM tropolone) is introduced into an electrochemical cell.

This base solution is homogenized with a magnetic stirrer, and the mercury is allowed to deposit for 10 minutes at a voltage of −1.0 V to form a thin layer mercury electrode. An amalgam of inorganic tin and tropolone forms on the surface of the said mercury electrode. A resting period (10 seconds) is given between the deposition step and the following stripping step so that the tin concentration within the said mercury electrode becomes uniform and the stripping can be performed in a stabilized solution. To identify the voltage region where tin deposition takes place, only the region from −0.4 to −0.8 V was chosen and the electrode was stripped. During this stripping step in which the voltage is scanned (linear sweep) from −0.4 V to −0.8 V, reoxidation of the deposited tin occurs at the standard electrode potential of tin-tropolone complex (from −0.6 to −0.65 V). This reoxidized tin returns to the solution from the electrode, which results in a current flow which manifests itself as a peak in the current-voltage curve.

After completion of measurements, the solution used was discarded and a cleaning solution was added with an applied voltage of 1.0 V to remove mercury and tropolone-tin complex from the surface of the glassy carbon main body. Once mercury and the complex were removed, the cleaning solution was discarded to prepare for another round of measurement. The general measurement procedures were used in the following examples as well.

Example 2

Figure 2:
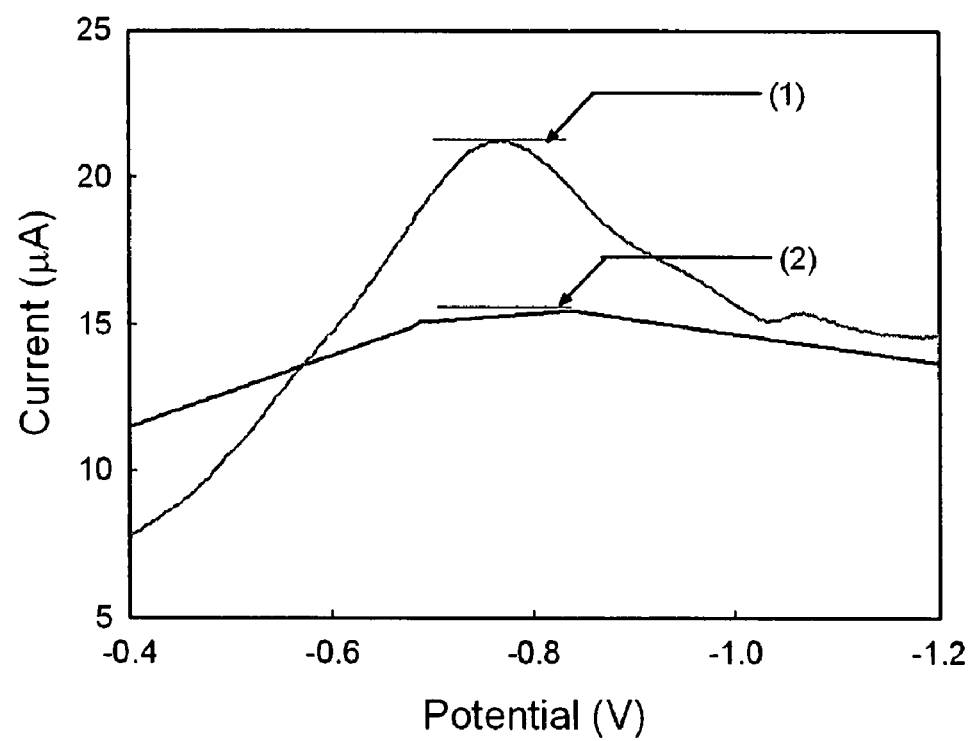
FIG. 2 is a graph showing the results of an experiment to confirm the presence of organotin compounds within a sample.
Figure 3:
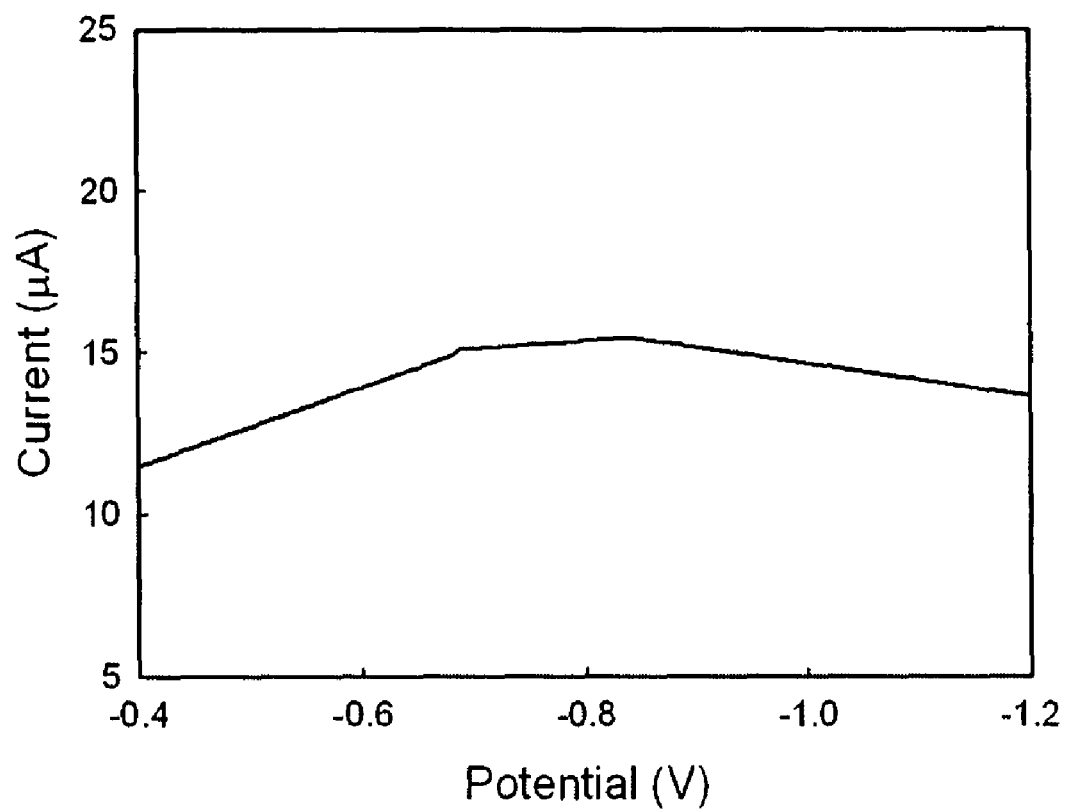
FIGS. 3 to 6 are graphs showing the results from a stripping voltammetry experiment on a sample containing inorganic tin compounds, listed according to the level of inorganic tin (the tin levels are as follows.
Figure 4:
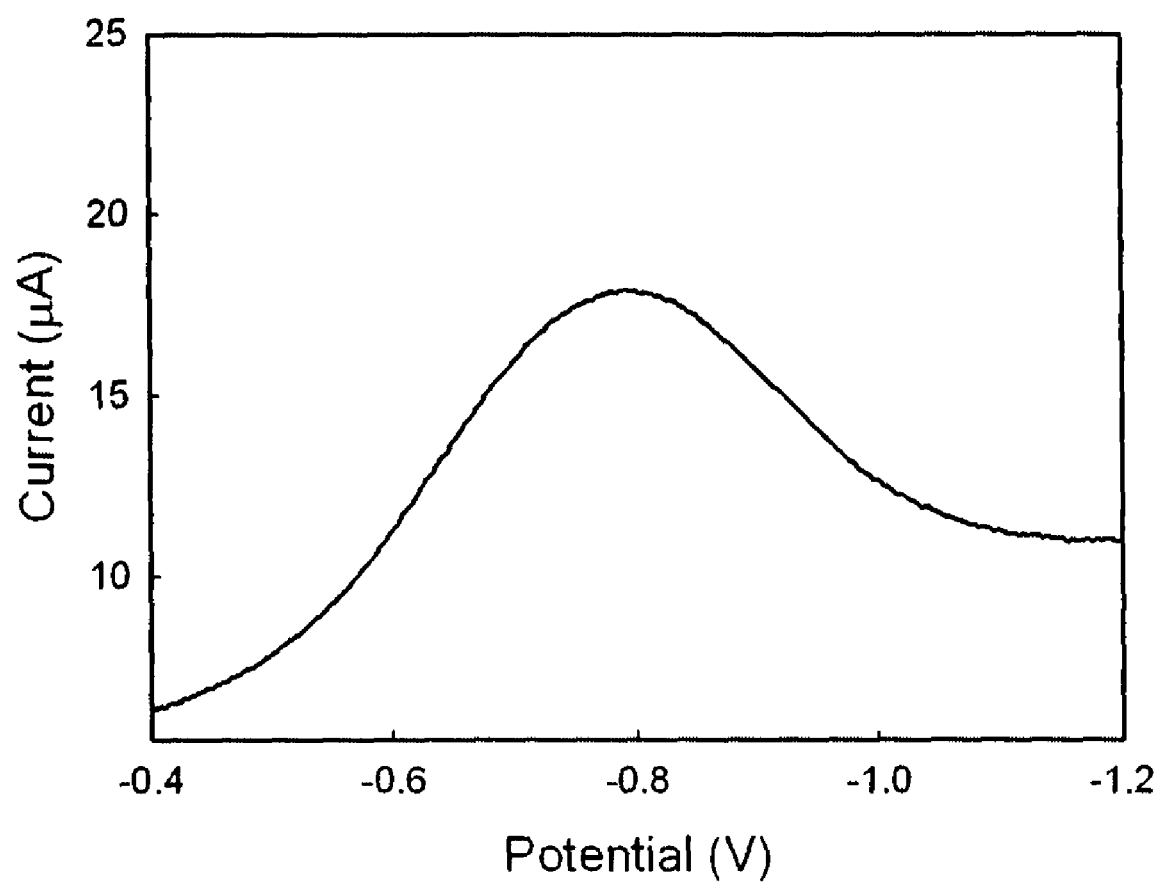
Figure 5:
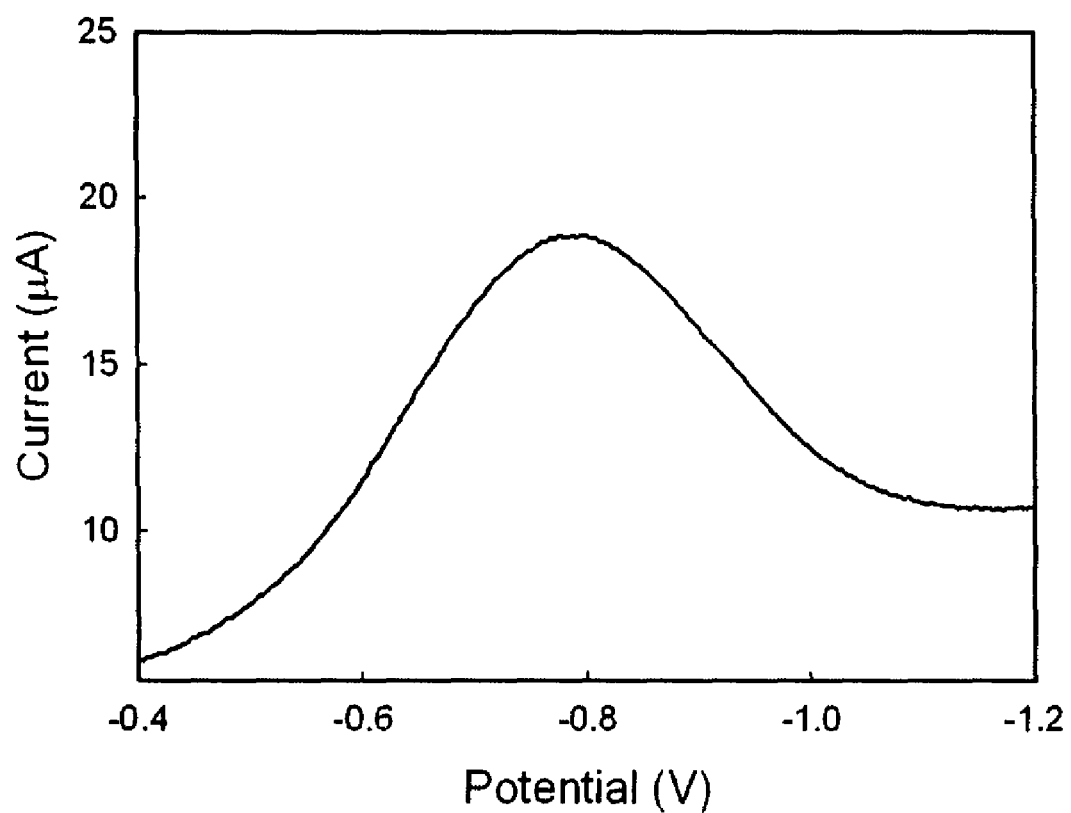
Figure 6:
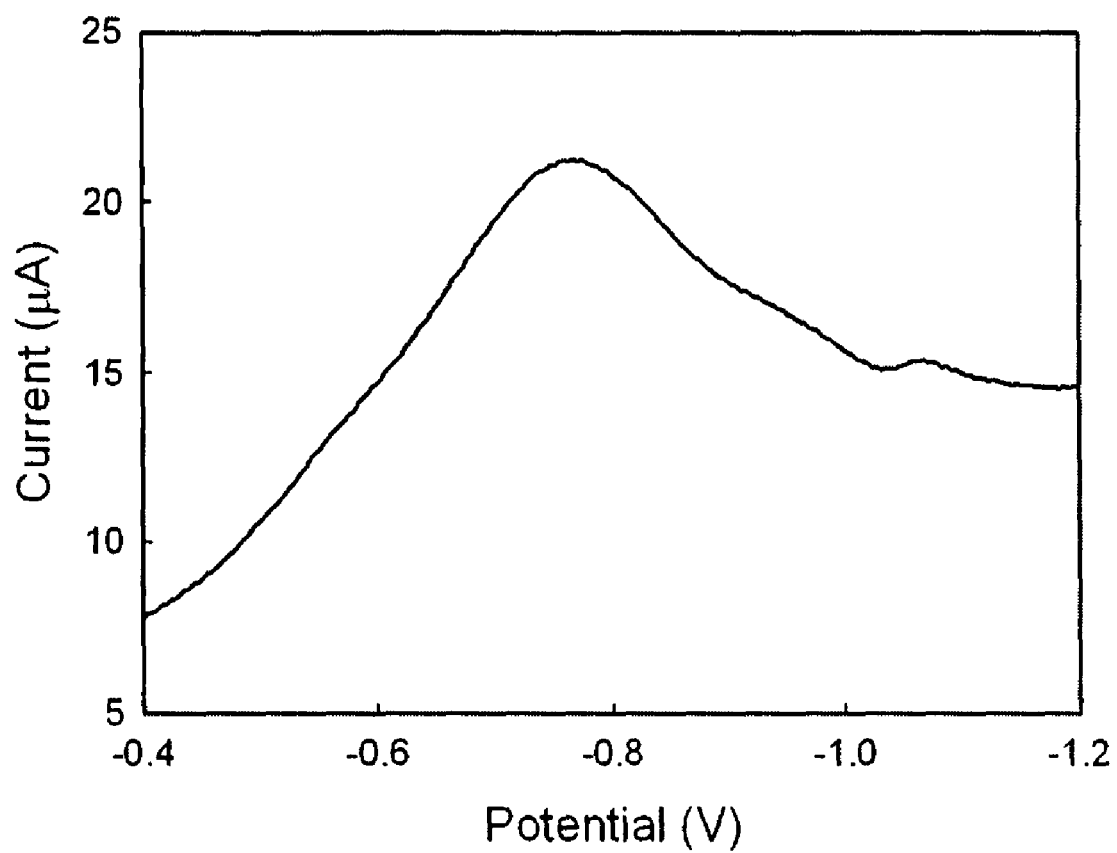

Confirming the Presence of Organotin Compounds in Samples (FIG. 2)

In the first experiment, the pH is adjusted to 2.8 and the sample is irradiated with UV to convert organotin compounds into inorganic tin. The UV-treated sample is then introduced into the reactor. In the second experiment, no UV irradiation is performed after pH adjustment and the pH-adjusted sample is introduced directly to the reactor for determining only the levels of inorganic tin originally present in the sample.

The sample thus introduced into the said reactor is then analyzed with adsorptive stripping voltammetry. The presence of organotin compounds in the sample is confirmed by the difference in the observed potential between UV-treated sample and non-treated sample. If no organotin is present, the potential difference between the two samples is 0.

Curve (1) of FIG. 2 corresponds to the UV irradiated sample in which organotin was converted into inorganic tin and curve (2) corresponds to non-irradiated sample. Since the difference in current values between curve (1) and curve (2) can be clearly observed, the presence of organotin in the sample is confirmed.

Example 3

Establishing a Standard for Quantitation of Organotin

Once the presense of organotin in the sample is confirmed by experiments such as example 1, a suitable substance containing inorganic tin is chosen as a standard for quantitating organotin. Solutions containing known concentrations of this standard are prepared. Adsorptive stripping voltammetry is performed on these inorganic tin sample solutions [0 ppm (FIG. 3), 22 ppm (FIG. 4), 35 ppm (FIG. 5) and 54 ppm (FIG. 6)] and the current is recorded. Next, a correlation is made between the observed voltammetric current and the level of inorganic tin (See the calibration curve in FIG. 7). This way, a calibration curve correlating the current reading and inorganic tin level is established, which in turn, can be used for quantitating organotin levels. If an unknown sample originally contained inorganic tin at least in part, the potential difference between the pH adjusted, UV-treated sample and the pH adjusted, non-UV-treated sample is measured and this difference is converted into organotin concentration.

Figure 7:
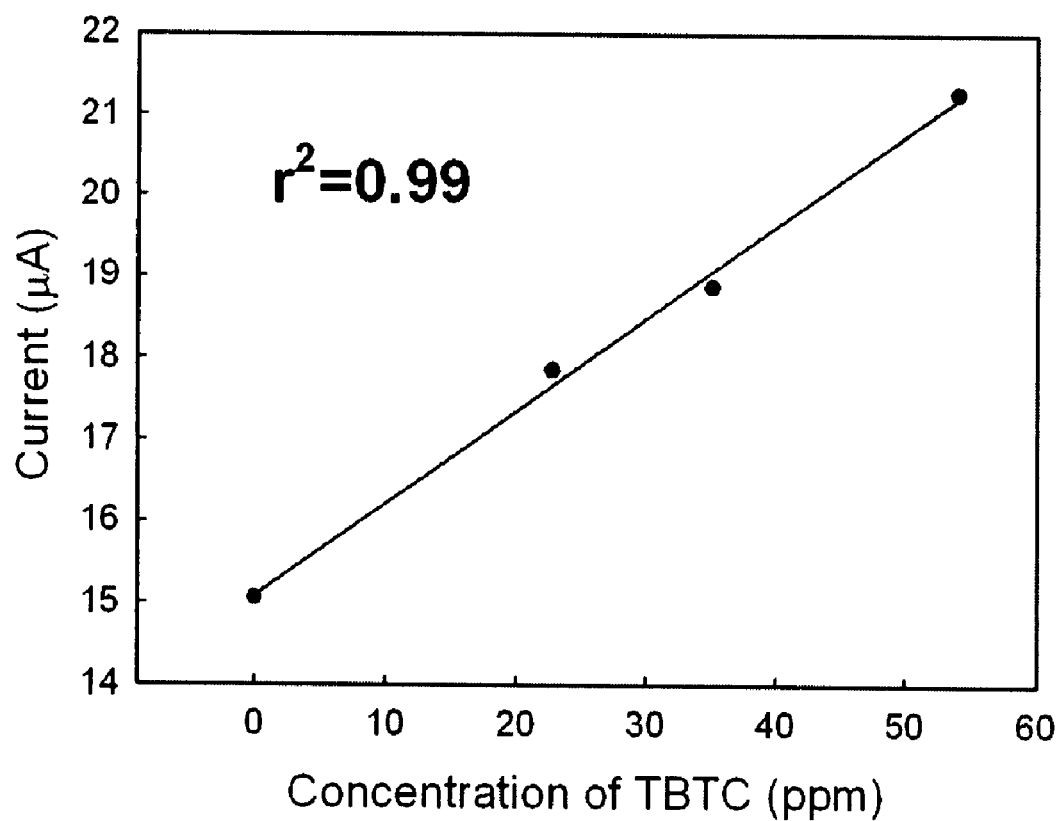
FIG. 7 is the calibration curve obtained from the data shown in FIGS. 3 to 6 which correlates the tin level with the current observed in stripping voltammetry experiments.
Figure 8:
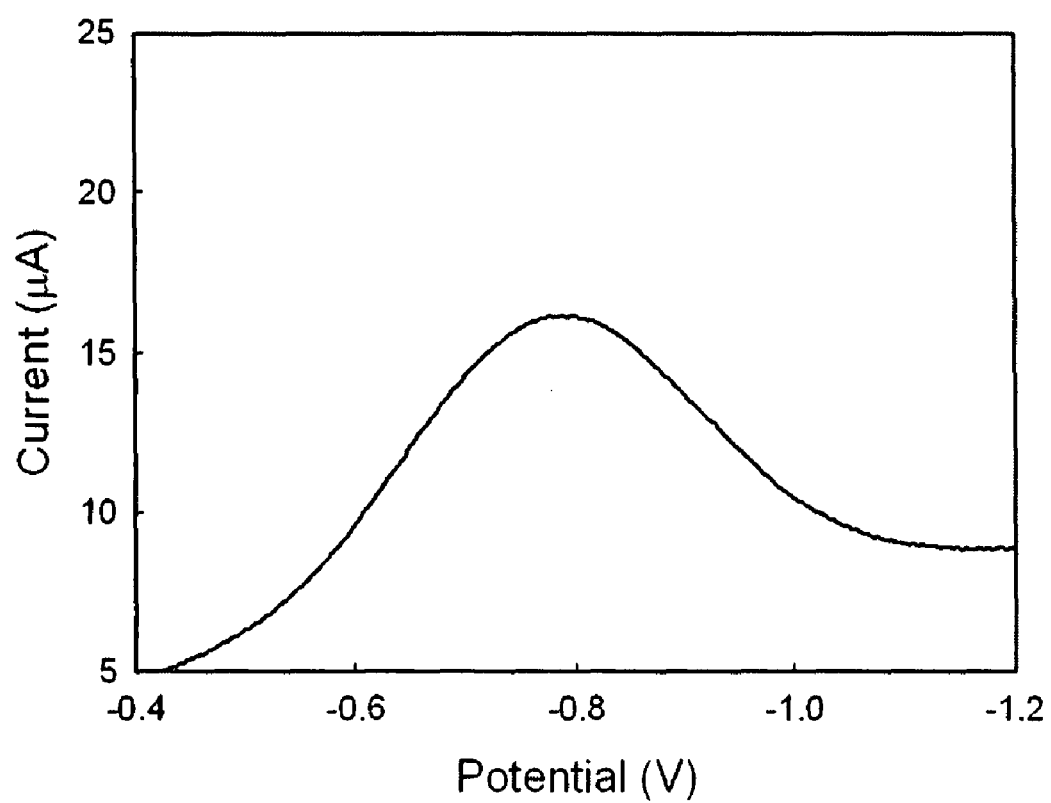
FIG. 8 shows the voltammetry data of a 10 ppm organotin sample. The measured current reading in this graph is 16.18 μA.
Figure 9:
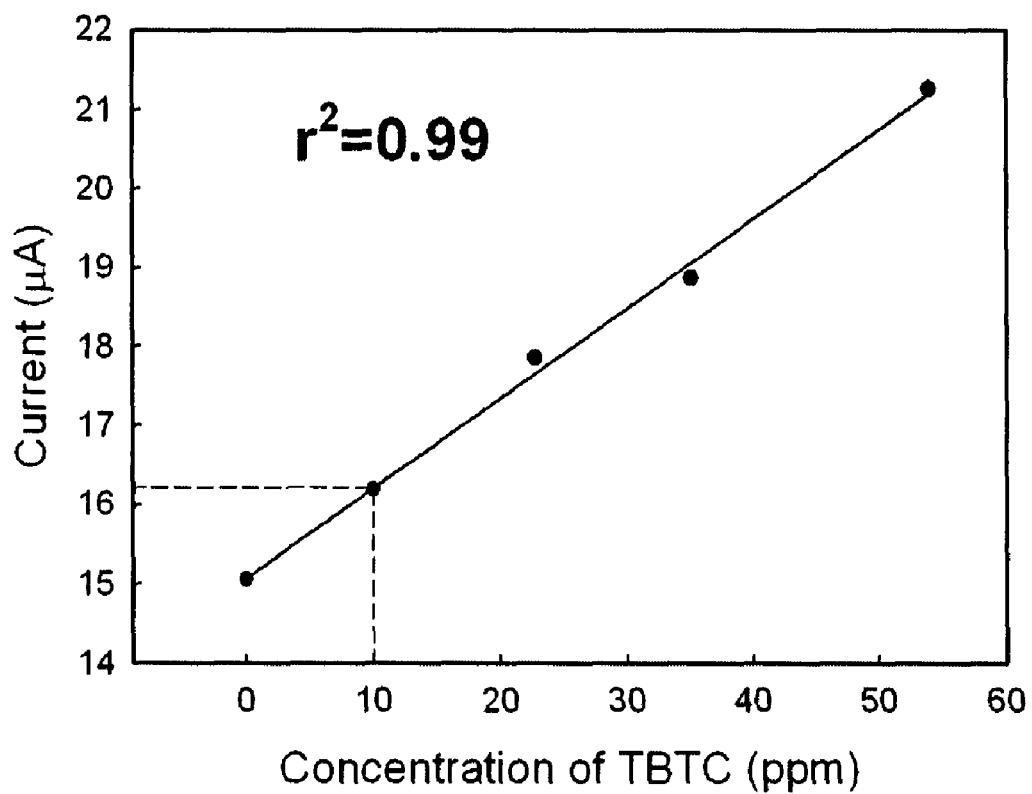
FIG. 9 demonstrates that the voltammetric current of 16.18 μA measured for the tin sample in FIG. 8 corresponds to a 10 ppm tin level of the calibration curve from FIG. 7.
Figure 10:
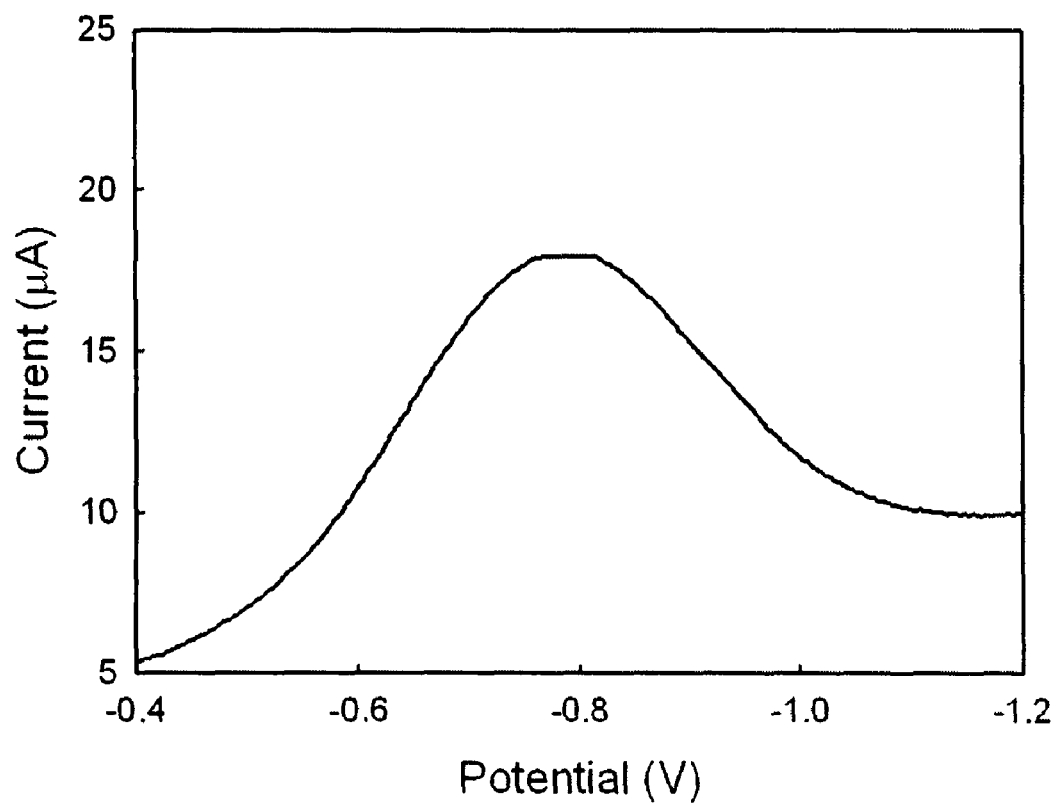
FIG. 10 is a graph that plots the data from a voltammetric measurement of an unknown sample. This sample was actual seawater taken in the vicinity of a shipbuilding plant.
Figure 11:
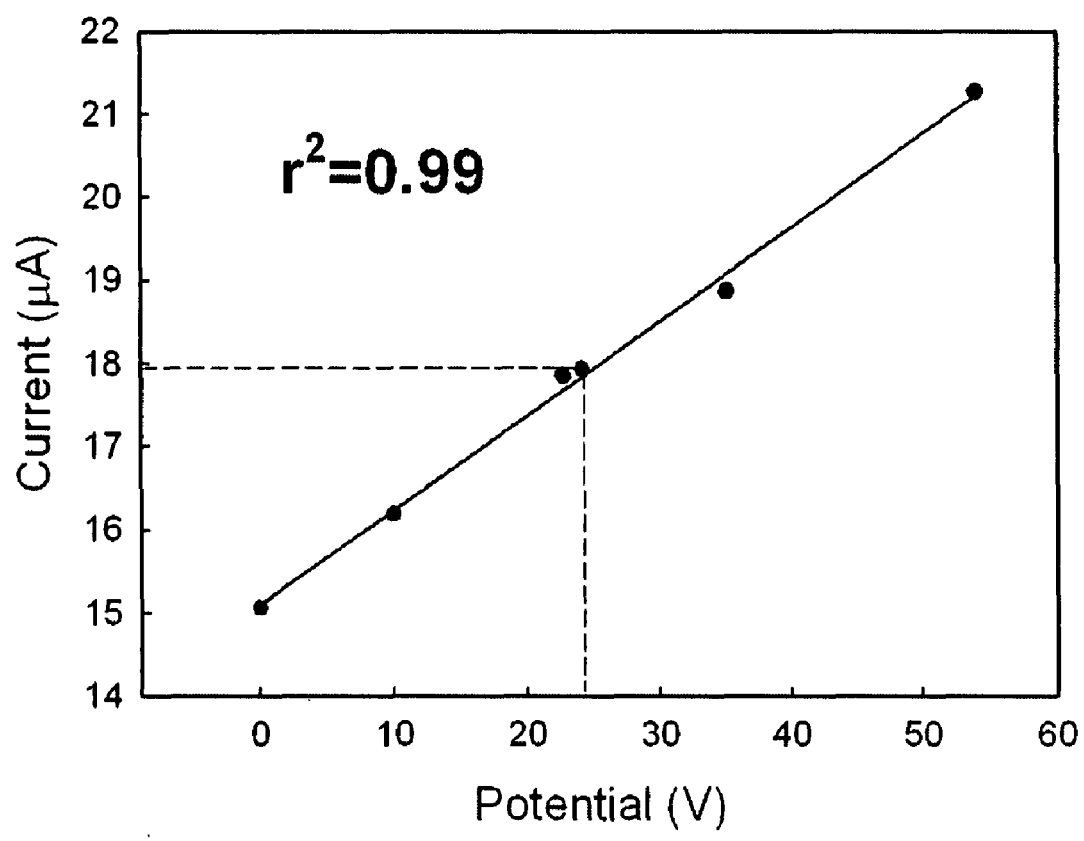
FIG. 11 demonstrates that tin concentration obtained by matching the current data from FIG. 10 against a corresponding point along the calibration curve is accurate. The concentration of the unknown sample was independently determined by gas chromatography.

The present inventors have made measurements on samples of various concentrations and looked for a correlation between the organotin level and voltammetric current. The correlation coefficient obtained was 0.99 as shown in FIG. 7; such high a result indicates a strong correlation. In short, the present inventors have confirmed in this experimental example, that by measuring voltammetric currents, the concentration of organotin compounds can be determined.

Example 4

Testing the Performance of the Inventive Measuring Apparatus for an Organotin Compound To test the sensitivity and accuracy of the inventive measuring apparatus, quantitative analysis of a sample containing tributyltin chloride (TBTC) was conducted. The sample pH was set to 2.8 and UV light was irradiated to convert TBTC into inorganic tin. The treated sample was diluted to 10 mg/L (FIG. 8) and a stripping voltammetry measurement was taken. The voltammetric current observed was calibrated against the calibration curve in FIG. 9. As evident from FIG. 9, the agreement between the calibrated organotin level from current measurement and the true level of organotin was excellent.

Example 5

Quantitation of Organotin in an Unknown Sample

The feasibility of the inventive measuring apparatus has been demonstrated in the previous examples. In this example, the inventive apparatus was applied to the analysis of a real sample (seawater and the precipitate collected 20 meters below the surface in the vicinity of a shipbuilding plant, FIG. 10). The organotin levels determined as such was compared with the value determined from GC (FIG. 11), a standard analysis method in the prior arts.

The voltammetric current for the seawater sample was 18.04 µA, which corresponds to a organotin level of 24.23 ppm in the calibration curve. The organotin level for the same sample determined by gas chromatography was in good agreement with the result from the inventive apparatus.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A method for analyzing tin compounds in liquid samples comprising the steps of:
    (a) measuring a voltammetric current for a first batch of an unknown liquid sample after acidifying said first batch by injecting acid so as to adjust the acidity of said first batch until a preset acidity value is reached;
    (b) measuring a voltammetric current for a second batch of said unknown sample after acidifying said second batch by injecting acid so as to adjust the acidity of said second batch until said acidity preset value is reached and irradiating said second batch with ultraviolet light after acidification; and
    (c) comparing the measured current values obtained in measuring steps (a) and (b); and
    (d) confirming the presence or absence of organotin compounds within the said unknown sample based on the compared measured current values.

2. The method according to claim 1, wherein the said preset acidity value is in the range of pH 2.5 to 3.5.

3. The method according to claim 2, wherein the said preset acidity value is pH 2.8.

4. A method for analyzing tin compounds in liquid samples comprising the steps of:
    (a) confirming the presence of an organotin compounds within an unknown sample by conducting the steps of claim 1 on a batch of the said unknown sample;
    (b) determining a concentration value of inorganic tin present in the said unknown sample, said determining comprising:
        i. obtaining a third batch of said unknown sample;
        ii. acidifying a liquid sample containing a known concentration of inorganic tin by injecting acid so as to adjust the acidity of said liquid sample until said preset acidity value is reached, resulting in an acidified liquid;
        iii. measuring a voltammetric current for the acidified liquid sample from step (ii);
        iv. repeating the steps of (ii) and (iii) for various other liquid samples of known concentrations of inorganic tin to establish a calibration curve correlating to voltammetric current measured for each of said various other liquid samples of known concentrations;
        v. acidifying said third batch of said unknown sample by injecting acid so as to adjust the acidify of said third batch until said preset acidity value is reached, resulting in an acidified third batch;
        vi. measuring a voltammetric current for the acidified third batch; and
        vii. determining the concentration of inorganic tin present in said unknown liquid sample by matching said voltammetric current measured in step vi) against said calibration curve of step (iv), and
    (c) acidifying a fourth batch of said unknown sample by injecting acid and converting organotin compounds within said fourth batch into inorganic tin upon completion of the acidification by irradiating ultraviolet light thereon, wherein the said fourth batch of the unknown sample has not been subject to steps (a) and (b) prior to being subjected to step (c) and wherein said acid injection continues until an acidity of the said fourth batch reaches said preset acidity value;
    (d) determining a combined concentration value of organic and inorganic tin for said fourth batch after step (c) by performing steps (vi) and (vii); and
    (e) subtracting the concentration value of step (b) from that of step (d).

5. The method according to claim 4, wherein the said preset acidity value is in the range of pH 2.5 to 3.5.

6. The method according to claim 5, wherein the said preset acidity value is pH 2.8.

* * * * *